United States Patent [19]
Simons

[11] Patent Number: 6,140,530
[45] Date of Patent: Oct. 31, 2000

[54] QUINIDINE CONJUGATES AND THEIR USE IN IMMUNOASSAYS

[75] Inventor: Donald M. Simons, Wilmington, Del.

[73] Assignee: Dade Behring Inc., Deerfield, Ill.

[21] Appl. No.: 08/827,139

[22] Filed: Mar. 27, 1997

Related U.S. Application Data

[62] Division of application No. 08/510,886, Aug. 3, 1995, abandoned.

[51] Int. Cl.[7] .................................................. C07C 269/04
[52] U.S. Cl. ............................................................ 560/159
[58] Field of Search ...................................... 560/160, 159

[56] References Cited

U.S. PATENT DOCUMENTS

| | | | |
|---|---|---|---|
| 4,341,865 | 7/1982 | Voss | 435/188 |
| 4,617,261 | 10/1986 | Sheldon, III et al. | 435/6 |
| 4,952,569 | 8/1990 | Simons | 424/88 |
| 5,288,709 | 2/1994 | Freiberg et al. | 514/29 |
| 5,288,749 | 2/1994 | Meyer et al. | 514/414 |

FOREIGN PATENT DOCUMENTS

| | | |
|---|---|---|
| 156287 | 10/1985 | European Pat. Off. . |
| 0 230 363 A2 | 7/1987 | European Pat. Off. . |
| 574000 | 12/1993 | European Pat. Off. . |
| 0 599 325 A1 | 6/1994 | European Pat. Off. . |
| 0 642 798 A2 | 3/1995 | European Pat. Off. . |
| 0 668 504 A1 | 8/1995 | European Pat. Off. . |
| WO A 85/00605 | 2/1985 | WIPO . |
| WO 91/16322 | 10/1991 | WIPO . |
| WO 93/07142 | 4/1993 | WIPO . |

OTHER PUBLICATIONS

Tod, et al. J. Pharmaceutical and Biomedical Analysis. "Comparison of Serum Hydoquinidine Determination by Fluorescence Polarization Immunoassay and Liquid Chromatography". vol. 8, pp. 279–282, 1990.

B. Erlanger. Methods in enzymology. "Preparation of Antigenic Hapten–Carrier Conjugates: A Survey". vol. 70, pp. 85–105. Academic Press, Inc., 1980.

Koehler, et al.; *Nature*; Continuous Cultures of Fused Cells Secreting Antibody of Predefined Specificity; 256:495–497; 1975.

Dextraze, et al.; *Clinical Toxicology;* Comparison of an Enzyme Immunoassay and a High Performance Liquid Chromatographic Method for Quantitation of Quinidine in Serum; 18:291–297; 1981.

Brinkley, Michael; *Bioconjugate Chem.;* A Brief Survey of Methods for Preparing Protein Conjugates with Dyes, Haptens and Cross–Linking Reagents; 3:2–13 (1992).

Zuckermann, et al.; *J. Med. Chem.;* Discovery of Nanamolar Ligands for 7–Transmembrane G–Protein–Coupled Receptors from a Diverse N–(Substituted)glycine Peptoid Library; 37:2678–2685; 1994.

Schlünsen, et al.; *Makromol. Chem.;* Spezifische Adsorbentien für das Peptidantibiotika synthetisierende Enzymsystem Gramicidin S Synthetase, 1; 188:3005–3016; 1987. (Translation of relevant compound attached).

Inagaki, et al.; *The Chem. Soc. of Japan;* Asymmetric Introduction in the Base–Catalyzed Reactions Using Polymer–Supported Quinines with Spacer Groups; 60:4121–4126; 1987.

Bachrach, et al.; *Eur. Polym. J.;* Attachment of Drugs to Polydimethylisoloxanes; 20:493–500; 1984.

*Primary Examiner*—Mary E. Ceperley
*Attorney, Agent, or Firm*—Linda M Buckley; Cara Z Lowen

[57] ABSTRACT

This invention relates to quinidine derivatives and immunogenic conjugates and reporter conjugates prepared therefrom. The immunogenic conjugates and reporter conjugates are useful for eliciting antibodies and for performing immunoassays for quinidine. A particle agglutination immunoassay for quinidine is also provided.

2 Claims, 3 Drawing Sheets

QUINIDINE CONJUGATES AND THEIR USE IN IMMUNOASSAYS

This application is a division of Ser. No. 08/510,886 filed Aug. 3, 1995, abandoned.

FIELD OF THE INVENTION

This invention relates to quinidine conjugates and their application to immunoassays for quantifying quinidine in a test sample, and, more particularly, to quinidine derivatives useful for raising anti-quinidine antibodies and for synthesis of conjugates with reporter reagents. This invention also relates to monoprotected hydrophilic diamine reagents useful for the synthesis of quinidine conjugates containing a hydrophilic linker.

BACKGROUND ART

Specific binding reactions, such as antibody-antigen interactions, have been used extensively in immunoassays to detect and/or quantify a variety of drugs or other compounds of interest present in biological fluids. Such immunoassays have been developed for the determination of polyvalent antigens, such as proteins, as well as haptens.

Haptens are by definition molecules too small to stimulate the production of antibodies when administered to an animal; that is, haptens by themselves are not immunogenic. However, it is well known in the art that haptens can be made imunogenic by covalently attaching (conjugating) them to an appropriate carrier molecule. Administration of such an immunogenic conjugate to an animal generally elicits the production of a spectrum of antibodies, some of which are directed against antigenic sites (epitopes) native to the carrier and some of which are directed against the attached hapten molecules. Appropriate carriers commonly contain poly(amino acid) segments and include polypeptides, proteins and glycoproteins. Specific examples of useful carriers are keyhole limpet hemocyanin (KLH), bovine serum albumin (BSA), γ-globulins and plant globulins (for example, pumpkin seed globulin).

A variety of chemistries have been used for preparation of the immunogenic hapten-carrier conjugates necessary for raising anti-hapten antibodies. Since the native carriers generally contain a substantial number of lysine residues, each of which contains a reactive amine group, one particularly useful process utilizes the reaction of a hapten or hapten derivative containing amine-reactive functionality with the carrier. An important aspect of this approach is that hapten or hapten derivatives functionalized with a carboxyl group are readily converted to an appropriate amine-reactive intermediate.

Quinidine, the hapten of interest here, is a significant pharmacological compound. Its value as an antiarrhythmic drug was discovered through the chance observation that malaria patients with atrial fibrillation were occasionally "cured" of their arrhythmia while under treatment with these drugs.

Quinidine

In the absence of liver and/or kidney disease, the biologic half-life of quinidine is about 6 hours. Part of the drug is excreted unchanged by the kidney and the remainder is metabolized by the liver to products that do not have antiarrhythmic activity. Quinidine affects the rate and rhythm of the heart through direct effects on the heart muscle and through indirect effects on the conduction system. Quinidine reduces the excitability, conduction velocity and contractility of the myocardium.

Quinidine frequently produces unwanted gastro-intestinal side effects, which are somewhat dose-related. Monitoring the plasma drug level provides information helpful in maintaining adequate therapeutic levels while minimizing undesirable side effects.

However, native quinidine does not contain the amine-reactive functionality described above, so that it is necessary to synthesize an appropriate quinidine derivative. The C-10–C-11 double bond present in quinidine offers a particularly attractive place to start.

Kobayashi et al. (Journal of Polymer Science: Polymer Letters Edition, vol. 20, 85–90, Functional Polymers 9. Asymmetric Catalysis by New Cinchona Alkaloid Derivatives. Effect of C(3) Substituent On Asymmetric Induction, John Wiley and Sons, Inc., [1982]) disclose the synthesis of cinchona alkaloid derivatives having an organothio group at the C-11 position of quinidine. However, none of the derivatives prepared contained functionality appropriate to the objectives of the present invention.

International PCT application having International Publication No. WO 91/16322, published Oct. 31, 1991, and International PCT application having International Publication No. Wo 93/07142, published Apr. 15, 1993, disclose the use of quinidine and quinine derivatives as asymmetric hydroxylation catalysts. The compounds disclosed include a derivative of quinidine in which the C-11 position of quinidine is derivatized with a sulfonyl or sulfonyl linkage as a critical control agent. Similarly, these derivatives do not contain functionality appropriate to the objectives of the present invention.

Specifically, none of references cited mention or suggest the preparation or use of quinidine derivatives for synthesis immunogenic conjugates or reporter reagents (e.g., particle reagents) useful in immunoassays for quinidine.

There is a need for quinidine conjugates and their application to immunoassays for quantifying quinidine in a test sample and, especially, to quinidine derivatives useful for raising anti-quinidine antibodies to enable timely, precise monitoring of quinidine levels.

SUMMARY OF THE INVENTION

This invention has as one embodiment compounds having the structure I, which can also be represented as the internal salt II, or isolated as an external salt III:

where x is 1–2, and A- is an anion such as chloride ion, 4-toluenesulfonate ion, 3-mercaptopropionate ion, etc. When x=2, the compound of structure I or II is designated 'QAD-1', an acronym for Quinidine Acid Derivative, No. 1. A suitable chemical name for this compound is 11-(2 carboxyethylthio)dihydro-quinidine.

A further embodiment is an immunogenic conjugate of the claimed compounds and a carrier, particularly where the carrier is selected from the group consisting of poly(amino acids), proteins and glycoproteins.

A further embodiment is a conjugate of the claimed compounds and a reporter reagent. A reporter reagent is defined as a reagent that possesses some chemical or physical property that permits the amount of reporter reagent in a sample to be readily quanitifed. Latex particles, fluorophores, chemiluminescent substances, chromophores, radioactive substances and enzymes are common reporter reagents. In a properly configured assay, conjugates of a drug or other compound of interest and a reporter reagent can be used to relate the amount of drug in a sample with the amount of (readily measured) reporter reagent in the sample.

A further embodiment is a conjugate of the claimed compounds and a reporter reagent, more particularly where the claimed compounds are conjugated to the reporter reagent via a hydrophilic linker.

A further embodiment is a class of monoprotected hydrophilic diamines useful for the introduction of a hydrophilic linker segment into conjugates of drugs and reporter reagents.

A further embodiment of the invention is an immunoassay for determining the presence and/or amount of quinidine in a test sample, the steps in which are:

(a) mixing together the reporter reagent comprising a conjugate of the claimed compound and a reporter, the test sample, and an agglutinating agent, and followed by (b) carrying out any known agglutination immunoassay format.

BRIEF DESCRIPTION OF THE DRAWINGS

The invention will be more fully understood from the following detailed description, taken in accordance with the accompanying drawings, which form a part of this application and in which.

DESCRIPTION OF THE INVENTION

This invention relates to quinidine derivatives, immunogenic conjugates prepared therefrom, antibodies elicted by the immunogenic conjugates, conjugates of quinidine to reporter reagents, and their use in immunoassays.

The invention is ultimately concerned with the preparation of two final reagents: anti-quinidine antibodies and quinidine-latex particles. Both final reagents are components of an assay system for determining the presence and amount of quinidine in body fluids.

In the present invention, a carboxyl-functionalized quinidine derivative is synthesized by reaction of a thiol-functionalized carboxylic acid with the double bond located between atoms C-10–C-11. The addition of a thiol to a double bond using free radical chemistry is known. For example, the derivative designated QAD-1 is made by the free radical addition of 3-mercaptopropionic acid (3-MPA) to the quinidine double bond using 2,2'-azobis (isobutyronitrile) (AIBN) as the initiating free radical source. The reaction can be visualized as taking place in several steps. In the scheme below, the dot represents an unpaired electron and QCH=CH$_2$ represents quinidine.

1. Radical generation (initiation).

2. Radical transfer from carbon to sulfur, forming a thiol radical.

3. Addition of thiol radical to the quinidine double bond.

4. Radical transfer from carbon to sulfur.

5. The reaction now cycles many times through Steps 3 and 4, converting the reactants to QAD-1 in satisfactory yield.

The carboxyl-functionalized quinidine derivatives of the present invention can be conjugated with a carrier to produce an immunogen. A first step entails the converstion of the carboxyl group to an amine-reactive group. Methods for converting carboxyl-functionalized reagents to amine-reactive reagents are well known to those skilled in the art. Formally, the hydroxyl group in the carboxylic acid group is replaced with an electronegative or electron-withdrawing atom or group, so that a partial positive charge is induced on the adjacent carbonyl carbon atom.

$$RC(=O)-OH \longrightarrow RC(=O)-X$$

Some structures of X that fulfill this requirement are shown in the following list:

—Cl, —Br, —F    Acyl halide

Anhydride or mixed anhydride

Isourea ester

Isouronium ester

-continued

Mixed phosphorus acid anhydride

Acyl phosphinate mixed anhydride

Mixed acyl pyrophosphate anhydride

Acyl borate mixed anhydride

Acyl azide

Imidazolide

Imidazolium derivative

Acylimidazolium derivative

Triazolide

1-Methylpyridinium-2-yl ester

4-Nitrophenyl ester

Trichlorophenyl ester

Pentachlorophenyl ester

Tetrafluorophenyl ester

Pentafluorophenyl ester

Nitrosulfophenyl ester

Trinitrosulfophenyl ester

Triazinyl ester

Benzoxalium ester

Thieno ester

In the present instance, disuccinimidyl carbonate is used to convert QAD-1 to the amine-reactive succinimidyl ester, which is then reacted with the lysine (amine) groups in the carrier to provide an immunogenic conjugate (immunogen). This immunogen can be used to elicit antibodies using known antibody producing and screening procedures. For example, the immunogen can be injected into appropriate animal hosts to stimulate the production of antibodies. The antibodies so produced can be harvested for direct use in specific binding reactions with the hapten or closely related analogs, or they can be first purified from animal serum by any of several known means, such as affinity chromatography. Alternatively the immune lymphocytes harvested from the injected host can be screened using the conjugates of this invention to select those cells which are responsive to the immunogenic conjugate. These can then be fused with appropriate myeloma cells, to produce hybridomas that are capable of producing monoclonal antibodies. Methods of cell fusion, selection and proliferation are well known and are generally modifications to the procedures of Kohler et al., *Nature*, vol. 256, 495–497 (1975). Preferably, the antibodies of the present invention are monoclonal antibodies prepared using hybridoma technology.

The anti-quinidine antibodies produced using the immunogenic conjugates of the present invention can be employed in any known immunoassay format utilizing the specific binding reaction between an antibody and its hapten to detect the presence and/or amount of free hapten in a test sample. Examples of such known immunoassay formats include homogeneous, heterogeneous, competitive and direct (non-competitive) formats.

A process of the present invention entails the coupling of the claimed compounds to a reporter reagent, particularly to latex particles. Preferred particles include those having a polystyrene core and a poly(glycidyl methacrylate) shell that has been cross-linked with ethylene glycol dimethacrylate. The preparation and use of such particles are described in U.S. Pat.. No. 4,480,042, issued to Craig et al., and hereby incorporated by reference. The epoxide groups on the surface of these particles react readily with amines, thiols, etc., a property that can be utilized to attach various compounds of interest to the latex particles. In particular, epoxide groups react with amine groups present in the hydrophilic diamine linkers used in the present invention. In this connection, it should be mentioned that latex particles functionalized with other amine-reactive groups-such as aldehydes, succinimidyl esters, and allylic or benzylic halogen compounds-are also suitable for use as reporter reagents in the present invention.

It is known to those skilled in the art that coupling two components of a conjugate pair by means of a highly hydrophilic linker (also sometimes referred to as a spacer or bridge) frequently improves the subsequent performance of conjugate in its intended function. Some examples of this effect are given in the following references: (a) W. A. Frey and D. M. Simons. Polyether polyamines as linking agents for particle reagents useful in immunoassays. U.S. Pat. No. 4,581,337, Apr. 8, 1986; (b) D. M. Simons, S. Y. Tseng and D. M. Obzansky. Method for specific binding assays using a releasable ligand. U.S. Pat. No. 5,332,679, DuPont, Jul. 26, 1994; (c) E. Akerblom, M. Dohlsten, C. Brynö, M. Mastej, I. Steringer, G. Hedlund, P. Lando and T. Kalland. Preparation and characterization of conjugates of monoclonal antibodies and staphylococcal enterotoxin A using a new hydrophilic cross-linker. *Bioconjugate Chem.* 4: 455–466 (1993); (d) E. Huber, D. Zdunek, C. Klein and R. Schenk. Hapten-Biotin-Konjugate und Ihre Verwendung. EP 0 451 810 A1, Apr. 10, 1991 (Boehringer Mannheim). It is postulated that the beneficial effects arise from a combination of two factors: decreased steric hindrance and low non-specific, non-covalent interaction of the hydrophilic linker with hydrophobic areas present in one or the other of the components of the conjugate or in other reagents which may added subsequently. In the present instance, the use of such a hydrophilic spacer improves the precision and accuracy of the quinidine assay.

Di- or polyamine reagents containing oxyethylene units are particularly suited for use as hydrophilic linkers. Some specific examples are:

H$_2$NCH$_2$CH$_2$OCH$_2$CH$_2$OCH$_2$CH$_2$NH$_2$
1,8-Diamino-3,6-dioxaoctane
DuPont code name: DA-10:
Trade name: Jeffamine EDR-148
Manufacturer or source: Texaco Chemical Co.
pKa (both amine groups are the same): 9.4
H$_2$NCH$_2$CH$_2$CH$_2$OCH$_2$CH$_2$OCH$_2$CH$_2$CH$_2$NH$_2$
1,10-Diamino-4,7-dioxadecane
DuPont code name: DA-12
Manufacturer or source: Tokyo Kasel, Inc., 911 N. Harborgate St., Portland, Oreg.

pKa (both amine groups are the same): 9.98
H$_2$NCH$_2$CH$_2$OCH$_2$CH$_2$OCH$_2$CH$_2$OCH$_2$CH$_2$NH$_2$
1,11-Diamino-3,6,9-trioxaundecane
DuPont code name: DA-13
Trade name: Jeffamine EDR-192
Manufacturer or source: Texaco Chemical Co.
pKa (both amine groups are the same): 9.4
H$_2$NCH$_2$CH$_2$0CH$_2$CH$_2$0CH$_2$CH$_2$0CH$_2$CH$_2$NH$_2$
1,13-Diamino-4,7,10-trioxatridecane
DuPont code name: DA-15
Manufacturer or source: Fluka
pKa (both amine groups are the same): 10.02

In the DuPont code names for the above materials, "DA" signifies diamine and the number indicates the number of atoms in the chain exclusive of the terminal hydrogen atoms. The lower non-specific, non-covalent intermolecular interaction inherent in molecules containing oxyethylene chains, relative to their all hydrocarbon analogs, manifests itself in the physical properties. For example, DA-10 is a liquid at room temperature, but its all-hydrocarbon analog, 1,8-diaminooctane, is a solid melting at 52° C.

The quinidine-hydrophilic spacer-reporter reagent conjugates of the present invention can be prepared in several ways. For example, a 3-step process can be used: (a) convert the carboxyl-functionalized drug derivative (such as QAD-1) to an amine-reactive derivative; (b) couple the amine-reactive drug derivative to one amine group of a hydrophilic diamine; and (c) contact the conjugate so prepared with an amine-reactive reporter reagent, thereby forming the desired drug-hydrophilic spacer-reporter reagent conjugate. Or, alternatively, (a) couple the amine-reactive reporter reagent and one amine group of a hydrophilic diamine; (b) convert the carboxyl-functionalized drug derivative to an amine-reactive derivative; and (c) combine the two reagents to form the desired drug-hydrophilic spacer-reporter reagent conjugate. In the process of the present invention, the carboxyl-functionalized QAD-1 is converted to the amine-reactive succinimidyl ester by means of the reaction with disuccinimidyl carbonate.

The two amine groups in each of the hydrophilic diamines described above have equal basicity, as reflected in the pK$_a$ values, and equal reactivity toward various amine-reactive reagents. The reaction of such diamines with a limited quantity of amine-reactive reagent always yields a mixture containing two reaction products plus unreacted diamine:

The mole-fraction of each of these components in the final reaction mixture is a function of the initial stoichiometry.

The theoretical distribution of the products is shown in Table 1:

TABLE 1

Theoretical Product Distribution
(mol-fraction) as a Function of Stoichiometry

| Component in Product | Mole Ratio of Reactants*: | | |
|---|---|---|---|
| | 1:1 | 2:1 | 3:1 |
| Monosubstituted diamine: | 1/2 | 3/8 | 5/18 |
| Disubstituted diamine: | 1/4 | 1/16 | 1/36 |
| Unreacted diamine: | 1/4 | 9/16 | 25/36 |

*Mole ratio of diamine to amine-reactive reagent

That quantity of amine-reactive drug derivative converted to disubstituted diamine is generally lost. This can be a major problem when this derivative is very expensive or difficult to synthesize in quantity. The theoretical loss of drug derivative as a function of stoichiometry is shown in Table 2:

TABLE 2

Theoretical Loss of Drug Derivative
As a Function of Stoichiometry

| Mole Ratio of Reactants* | Loss of Drug Derivative, % |
|---|---|
| 1:1 | 50 |
| 2:1 | 12.5 |
| 3:1 | 5.6 |

*Mole ratio of diamine to amine-reactive reagent

Product mixtures and the associated loss of valuable drug derivative can be avoided by carrying out the reaction of the amine-reactive drug derivative with a half-protected hydrophilic diamine, that is, with a hydrophilic diamine in which one amine group has been previously been blocked with a suitable protective group. Said protective group must remain intact during all conditions utilized in the reaction with the amine-reactive drug derivative, but must readily removable subsequently. In the present instance, tert-butoxycarbonyl (Boc) group has been found to be a satisfactory protective group. A process that provides the desired half-protected intermediate, free of both diprotected diamine and unreacted diamine, has been developed. The process entails the following successive steps:

(a) Reacting di-tert butyl dicarbonate ('Boc anhydride') with excess hydrophilic diamine in an aqueous/organic medium in the presence of sodium hydroxide.

(b) Removing of the organic solvent to convert the system to an essentially aqueous phase.

(c) Reducing the pH of the aqueous phase to a level that ensures that essentially all of the residual amine groups are in the protonated form.

(d) Extracting the aqueous phase with a water-immiscible organic solvent to remove nonbasic material.

(e) Raising the pH of the aqueous phase to a level that ensures that half or more than half of the residual amine groups are present are in the unprotonated form.

(f) Adding of salt to aqueous phase.

(g) Extracting the aqueous phase with a water-immiscible organic solvent.

(h) Separating the organic phase.

(i) Removing the solvent from the organic phase to leave the desired product.

An illustrative process for using the monoprotected diamine for synthesizing a drug-hydrophilic spacer-reporter reagent conjugate, utilizing a the half-Boc hydrophilic diamine intermediate is as follows:

(a) Convert the carboxyl-functionalized drug derivative to an amine-reactive derivative.

(b) couple the amine-reactive drug derivative the free amine group of the monoprotected hydrophilic diamine.

(c) Remove the protective group.

(d) Liberate the free amine from the amine salt.

(e) React the drug-hydrophilic linker conjugate so prepared with an amine-reactive reporter reagent (here, epoxide-functionalized latex particles).

Steps (d) and (e) can generally be carried out together in the same pot.

The drug-hydrophilic linker-reporter reagent conjugates here described can be employed in any known immunoassay format that uses a reporter to detect the presence and/or amount of a drug, such as quinidine, in a test sample.

The preferred immunoassay format using the drug-hydrophilic linker-particle reporter reagents (particle reagents) of the present invention is a particle-enhanced turbidimetric-inhibition immunoassay (PETINIA). This immunoassay format utilizes very small latex particles (e.g., 70 nm) to which have been attached a drug or other compound of interest. When viewed with monchromatic light having a wave-length (e.g., 340 nm) larger than the diameter of the suspended particles, e.g., the suspension is essentially transparent. Under optimal conditions, addition of antibody specific for the drug on the particles will cause the particles to aggregate. These aggregates are large enough to scatter light, which causes the suspension to become turbid. When a sample containing free drug is included, free drug competes with particle-bound drug for antibody, thereby inhibiting both the rate and extent of aggregation. This provides the basis for quantifying the amount of drug in the sample. Specifically, the quinidine-hydrophilic spacer-particle reagents and the anti-quinidine antibodies of the present invention enable a rapid, precise and accurate PETINIA method for determining the amount of quinidine present in biological fluids.

Other examples of known immunoassay formats which can be employed using the reporter reagents of the present invention include direct agglutination particle-based immunoassays, enzyme-linked immunosorbent immunoassays, and fluorescence-based immunoassays.

The following examples illustrate the invention:

EXAMPLE 1

Synthesis of a Quinidine Derivative (OAD-1)

A 250-mL two-necked flask, equipped with a magnetic stirrer, heating mantle, reflux condenser, and an inlet and exit for dry nitrogen, was thoroughly flushed with dry nitrogen and charged with 13.00 g (0.040 mol) of quinidine (Aldrich Chemical Co., Inc. Wisc.), 80 mL chloroform (VWR Scientific, Inc., N.J.), and 14 mL (0.16 mol) 3-mercaptopropionic acid (Aldrich Chemical Co., Inc., Wisc.). Azobis(isobutryronitrile) (660 mg; Polysciences, Inc., Pa.) was added, and the mixture refluxed for 12–15 hours. At the end of this period and additional azobis (isobutyronitrile) (550 mg) was added and the refluxing continued for and 12–15 hours.

The solution was cooled to room temperature and then added dropwise to 700 mL of stirred, anhydrous ether. A gummy precipitate separated. The flask was cooled in an ice-bath for about 30 minutes, and the ether layer then decanted. The residue was extracted three times with boiling ether (500 mL each time), which transformed it to a fine powder (weight, 18 g). Analysis for thiol content indicated that the product at this point contained a substantial amount of the 3-mercaptopropionic acid (3-MPA) salt of QAD-1: 0.594 pmole of thiol per mg of sample (=0.0594 mole/100 g), which corresponds to 73 mole % QAD-1 internal salt and 23 mole % QAD-1:3-MPA external salt.

The impure product was dissolved in 80 mL of chloroform, and the solution covered with 250 mL of water. A pH electrode was inserted in the aqueous layer, the mixture stirred gently, and solid sodium bicarbonate added cautiously until the pH stabilized at 7.0–7.2. The chloroform layer was separated, dried with magnesium sulfate, and added dropwise to 650 mL of stirred, anhydrous ether. The product separated as a fine, white solid and was collected by filtration. Weight, 15.3 g. Thiol analysis showed that this material contained 0.042 pmole of thiol per mg of sample.

The material was now refluxed in 100 mL of ethanol for 30 minutes. (Note: it did not dissolve completely.) The mixture was then chilled in an ice bath for 2–3 hours, and the product collected by filtration. Weight, 11.7 g (75% of theory). Thiol content was 0.030 pmole of thiol per mg of sample (=0.003 mole/100 g), corresponding to a composition of 98.7 mole % QAD-1 internal salt and 1.3 mole % QAD-1:3-MPA external salt.

QAD-1 can be converted to the 4-toluenesulfonate external salt by dissolving it in chloroform and adding the solution to a mixture of ethanol and ether containing the theoretical amount of 4-toluenesulfonic acid.

EXAMPLE 2

Preparation of Quinidine-Protein Conjugates

Proteins used were keyhole limpet hemocyanin (KLH), rabbit γ-globulin (RaIgG), pumpkin seed globulin (PSG), and ovalbumin (all from Sigma Chemical Co., Inc., Mo.). KLH, RaIgG and ovalbumin solutions were prepared by stirring the protein (150 mg) stirred in 25 mL of 150 mM sodium bicarbonate solution for several hours and centrifuging to remove any insoluble material (if necessary). PSG solution was prepared by dissolving PSG (105 mg) in 25 mL of 150 mM sodium bicarbonate containing 4M sodium chloride.

Preparation of a stock solution of QAD-1 succinimidyl ester. QAD-1 (120.45 mg), disuccinimidyl carbonate (78.83 mg), 3344 µL of dry dimethylsulfoxide and 45 µL of triethylamine were combined in a tared vial. The total weight of solution was 3.963 g. The solution was allowed to stand at room temperature for 1.5 hours. The density of the solution, determined by weighing a 1000-µL aliquot, was 1.0893 mg/µL. If one assumes that the reaction is quantitative, the concentration of the QAD-1 succinimidyl ester is $(120.45 \times 1.0893)/(430.56 \times 3963) = 7.69 \times 10^{-5}$ mmol/µL. conjugate synthesis. QAD-1 succinimidyl ester stock solution was added to each protein solution in the quantities indicated: KLH (878 µL); PSG (878 µL); ovalbumin (878 µL); and RaIgG (750 µL). The solutions were allowed to stand overnight, then dialyzed against 3 changes of 150 mM sodium bicarbonate and 3 changes of phosphate-buffered saline. At the conclusion of the dialysis, the solutions had the following appearance: KLH conjugate, slightly turbid; γ-globulin conjugate, contained some precipitate; RaIgG conjugate, contained much precipitate (due to low salt concentration); ovalbumin conjugate, clear.

EXAMPLE 3

Brief Summary of Immunization and Antibody Testing Protocol

Three sets of five female BALB/c mice were injected with three doses of quinidine-KLH conjugate and quinidine-rabbit γ-globulin conjugate and quinidine-PSG conjugate, respectively. Each dose consisted of the appropriate conjugate emulsified with complete Freund's adjuvant on day zero and incomplete Freund's adjuvant on days 28 and 56. The mice were bled on days 42 and 70 post priming immunization.

Figure 1:
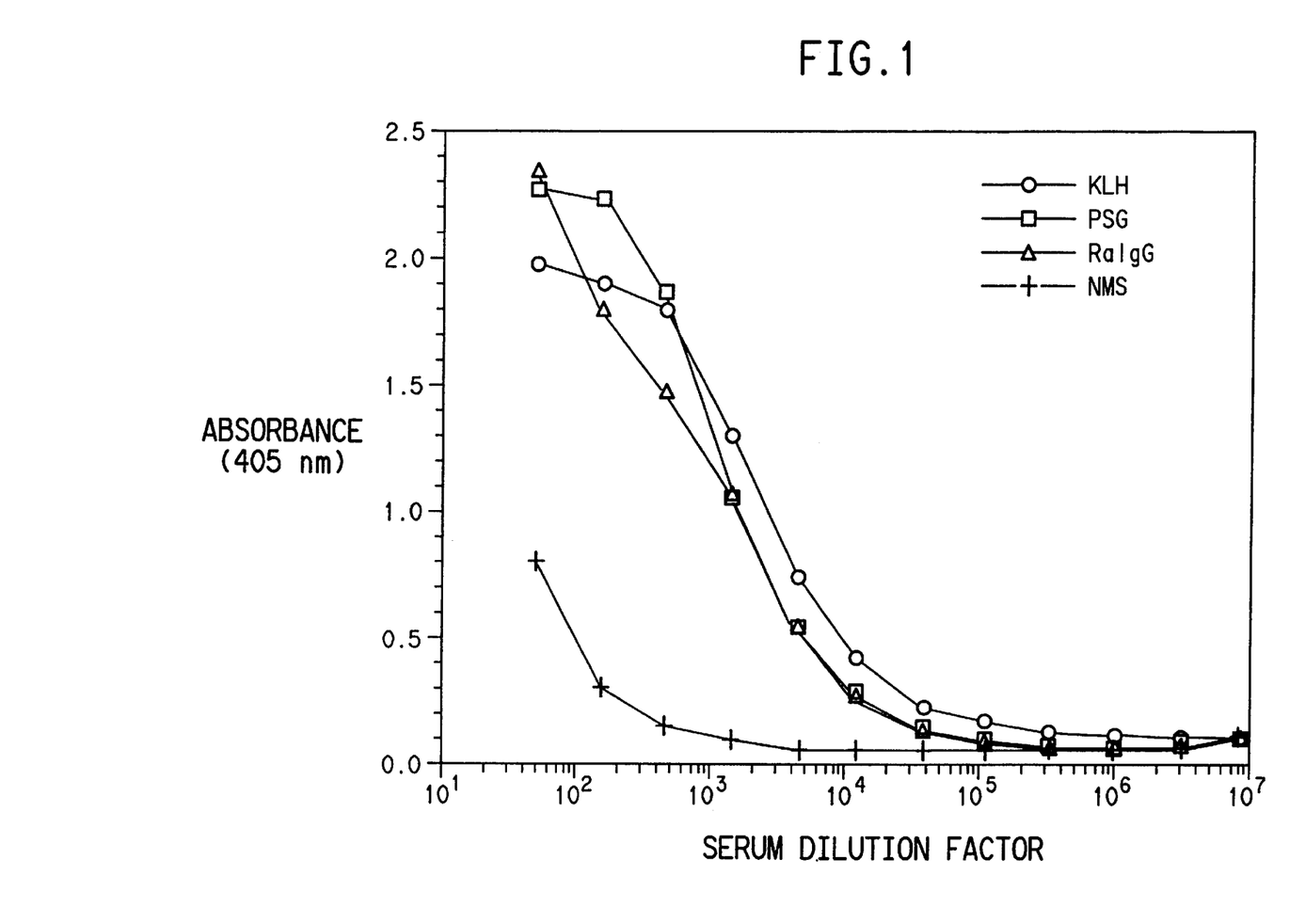
FIG. 1 shows that mice immunized with various QAD-1 protein immunogenic conjugates produced anti-quinidine antibodies. This figure is more explicitly discussed in Example 3.

Mouse IgG titers to quinidine were determined by an ELISA method. Plastic microtiter plates (Immulon II, Dynatech, Inc., Va.) were coated with quinidine-ovalbumin conjugate (6 mg/mL in 0.1M carbonate, pH 9.6), 50 µL/well, at room temperature for 3 hours and washed 3 times with 10 mM phosphate buffered saline (PBS). Antisera were diluted in PBS containing 1% BSA and 0.05% Tween 20 (PBT) (Sigma Chemical Co., MO) and incubated with the antigen-coated plates for 1 hour at 37° C. The plates were washed three times with PBS, and incubated for 1 hour at 37° C. with 50 µL/well of anti-mouse IgG rabbit immunoglobulin (gamma chain specific) labeled with horse radish peroxidase (Zymed Co., catalog no. 61-6020, 1:1000 in PBS containing 0.05% Tween 20). The wells were washed 3 times with PBS, and the presence of mouse IgG detected by adding 100 µL/well of the peroxidase substrate ABTS (2,2'-azino-di-(3-ethylbenzthiazoline sulfonate), diammonium salt) (Kierkegaard & Perry Co., Md., catalog no. 50-66-1), allowing to stand for 20 minutes at room temperature, and then reading the light absorbance at 405 nm. Results (see FIG. 1) with serum drawn on day 42 showed that all three conjugates elicited the production of quinidine-specific IgG antibodies after two doses of immunogen. (In FIG. 1, the abbreviation 'NMS' signifies non-immune serum, used as a control.)

Figure 2:
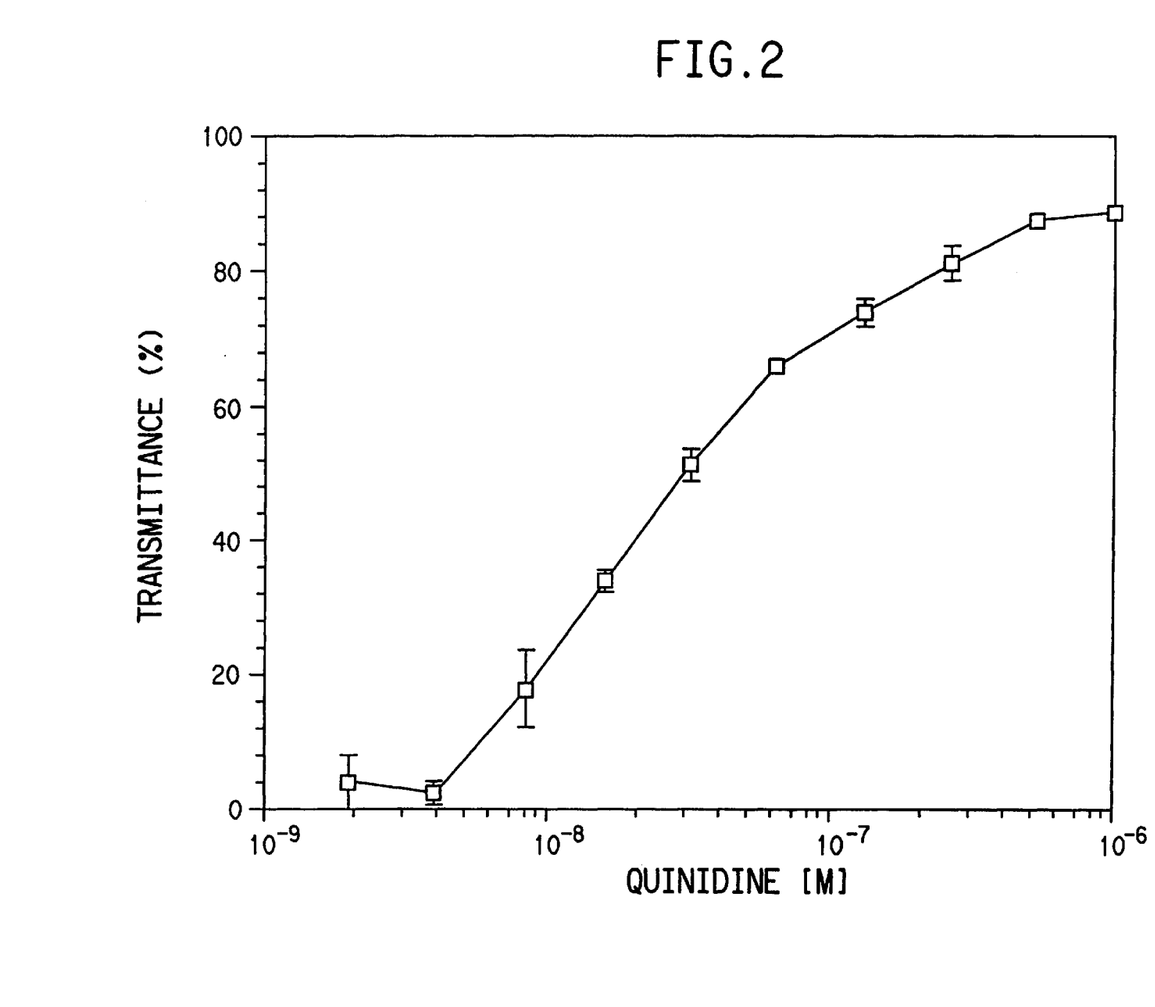
FIG. 2 is plot of data from a turbity-inhibition test and shows that free quinidine in solution competes with particle-bound quinidine for a limited quantity of antibody. This figure is also discussed in more detail in Example 3.

Reactivity of the mouse sera to free quinidine was determined by a particle-enhanced turbidimetric inhibition immunoassay (PETINIA). Latex particles having quinidine covalently coupled to their surface (quinidine particle reagent; QPR) were prepared using substantially the same procedure as that described in Example 6, below. The quinidine particle reagent (QPR) was diluted 1:100 in a buffer solution (PGP buffer) consisting of 100 mM phosphate, pH 6.9, 0.4% GAFAC RE-610, 4% polyethylene glycol 8000. Pooled antisera from mice immunized with quinidine-KLH conjugate (day 70) and quinidine (Sigma Chemical Co., MO; 10 mg/mL in DMSO) were diluted in PGP buffer. The assay was initiated by mixing 50 µL of diluted mouse serum (1:200) with 200 µL diluted quinidine particle reagent (QPR) (1:1000) in wells of a 96-well, flat-bottomed microtiter plate. Aggregation of the quinidine particle reagent by the mouse serum was inhibited by incorporating free quinidine into the diluted quinidine particle reagent prior to mixing with the antiserum. FIG. 2 shows the transmittance (%) versus the molar concentration of quinidine in the sample. The data demonstrate that mice immunized with the quinidine-protein immunogenic conjugates described in this invention produce antibodies that bind free quinidine in solution.

EXAMPLE 4

Preparation of a MonoBocylated Hydrophilic Diamine:Boc-DA-10

A 2-liter flask equipped with mechanical stirrer, thermometer and dropping funnel and cooled in an ice bath was charged with 68 g (0.458 mole) of DA-10, 230 mL of water, 460 mL of dioxane and 229 mL of 1N NaOH. The mixture was stirred until the temperature dropped below 10° C. The solution was stirred vigorously and Boc anhydride (50 g; 0.227 mole) added dropwide, while the temperature in the flask was kept below 10° C. After the addition was complete, the mixture was allowed to warm to room temperature and stand overnight.

Most of the dioxane was removed from the reaction mixture in the rotary evaporator, which resulted in the separation of an oily layer. The mixture was adjusted to pH 7 with 1M sodium bisulfate (about 730 mL required) and extracted three times with 100 mL-portions of ether. The ether extracts were discarded.

The pH of the aqueous phase was adjusted to 9.4 with 50% sodium hydroxide solution, 175 g of sodium chloride added (approximately half-saturation), and the brine solution extracted three times with 100-mL portions of chloroform. The pH was readjusted to 9.4 after each extraction, if necessary. The chloroform extracts were combined and dried over magnesium sulfate. The chloroform was removed as completely as possible in a rotary evaporator with the water bath temperature allowed to rise to 45° C. as this step neared completion. The residue weighed 25.74 g (theory=42.6 g); the yield (crude) was 60.4%. The amine content as determined by acid titration is shown in Table 4.

TABLE 4

Acid Titration of Boc-DA-in (in Duplicate)

| | Product from Final Extraction | |
|---|---|---|
| | a | b |
| Sample Wt., mg | 217 | 241 |
| 0.0992 HCl, mL | | |
| Actual | 7.689 | 8.515 |
| Theory* | 8.81 | 9.78 |
| Purity**, % | 87.3 | 86.3 |
| Yield, Pure Basis, % | 52.7 | 52.1 |

*Theory is the calculated value for pure Boc-DA-10, FW = 248.3
**Impurities consist of traces of chloroform, t-butyl alcohol, etc.

EXAMPLE 5

Preparation of a Quinidine-Hydrophilic Linker Conjugate

Method A. Direct Coupling of QAD-1 to DA-10

Stoichiometry: DSC/QAD-1 mole ratio 1.10; DA-10/QAD-1 mole ratio=3.00.

Solution 1. QAD-1 (107.65 mg, 0.2500 mmole) and disuccinimidyl carbonate (DSC; 70.46 mg, 0.2750 mmole) were placed in a 4-mL vial, 3.0 mL of dry DMSO added, and the mixture agitated until everything dissolved. Triethylamine (38 µL) was then added and the solution to stand at room temperature for one hour. (The vial cap was loosened periodically to release any pressure.)

Solution 2: A 12-mL vial+cap was labeled and tared to the nearest milligram. DA-10 (111.2 mg, 0.7503 mmole), 1.25 mL of DMSO and a magnetic stirring bar were added to the vial.

Solution 3: Solution 2 was stirred vigorously and Solution 1 added in discreet drops, allowing each drop to mix uniformly before the next one was added. The vial was rinsed with four 250-µL aliquots of dry DMSO to ensure quantitative transfer, and the final solution stirred for one hour. The magnetic stirring bar was raised above the level of the liquid in the vial (using an external magnet), rinsed with fresh, dry DMSO (1.00 mL total), and then removed from the vial. The vial and its cap were placed on a balance and the total weight of the contents adjusted to 7.646 grams by adding dry DMSO. The quantities of reagents were chosen to give a final conjugate concentration of about $3 \times 10^{-5}$ mmol/µL, based on the assumptions that all reactions are quantitative and that the theoretical distribution of mono- and disubstituted amines pertains.

Method B. Coupling of QAD-1 to Boc-DA-10 and Deprotecting

QAD-1 (107.65 mg, 0.2500 mmole) and triethylamine (38 µL) were dissolved in 2 mL of chloroform. Disuccinimidyl carbonate (DSC; 70.46 mg, 0.2750 mmole) was dissolved in 2 mL of acetonitrile. [Note: DSC is not soluble in chloroform.] The QAD-1 solution was added dropwise to the vigorously stirred DSC solution. Stirring was continued for 3 hours after the addition was complete, and a solution of Boc-DA-10 (62.08 mg; 0.2500 mmol) and triethylamine (38 µL) in 2 mL of acetonitrile was then added all at once. This combination was stirred for 3 hours, and then evaporated to dryness under reduced pressure. Ten mL of a 1:1 methylene chloride/trifluoroacetic acid was add to the residue, the mixture stirred for 30 minutes, and then evaporated to dryness under reduced pressure. The residue was dissolved in 8250 µL of dimethylsulfoxide. The quantities of reagents were chosen to give a final conjugate concentration of about $3 \times 10^{-5}$ mmol/µL, based on the assumption that all reactions are quantitative.

EXAMPLE 6

A. Quinidine-Hydrophilic Linker-Reporter Reagent Conjugate (Quinidine Particle Reagent: QPR):

Coupling of QAD-1-DA-10 Conjugate to Epoxide-Functionalized Latex Particles

Definitions: PRM (particle raw material) is a polymer latex in which the particles consist of a polystyrene core overcoated with crosslinked poly(glycidyl methacrylate), prepared as described in U.S. Pat. No. 4,480,042, issued to Craig et al. and incorporated by reference. GAFAC is GAFAC RE-610, formerly sold by the GAF Corporation, but now available from Rhone Poulenc, Collegeville, Pa., under the name of Rhodafac RE-610. Coupling buffer is 100 mM sodium carbonate/bicarbonate, pH 9.5. Wash buffer is 15 mM sodium phosphate containing 1% GAFAC, pH 7.4. Storage buffer is 15 mM phosphate containing 0.5% GAFAC, pH 7.4.

The following reagents were added sequentially to a 50 mL test tube reactor: 8.04 mL deionized water, 10 mL coupling buffer, 3.6 mL PRM (solids content, 20.3%; particle size, 70 nm), 1.25 mL 10% GAFAC, 1.8 mL (typically) of quinidine-hydrophilic linker conjugate (from Example 5, A or B), and 0.32 mL of a aqueous 10% DA-10 solution. The pH of the solution was adjusted to pH 9.5 and the reaction tube incubated at 70° C. for 18 hours. The resulting quinidine-hydrophilic linker-reporter particle reagent was separated by centrifugation for 2 hours at 5° C. (Sorvall RC28S, 27500 rpm on F28/13 rotor). The supernatant liquid was decanted and the particle reagent pellet suspended in 25 mL of the wash buffer. The centrifugation/wash step was repeated twice again and the final particle reagent pellet re-suspended in 25 mL of storage buffer This reagent, designated QPR, has a 3% solids content.

B. Assay Using Ouinidine Particle Reagent (QPR)

Definitions: Assay buffer is mM phosphate buffer, 0.4% GAFAC, pH 7.0, 0.002% thimerosal (ethylmercurithiosalicylic acid, sodium salt) (Aldrich Chemical Co., Inc. WI). Particle working solution is prepared by diluting quinidine particle reagent (QPR; 3% solids) 1:80 with assay buffer. Antibody stock solution is a purified anti-quinidine monoclonal antibody prepared in house, using known standard hybridoma techniques substantially the same as those disclosed by Kohler and Milstein, *Nature*, 256: 495–497 (1975). Antibody diluent is 50 mM phosphate buffer, 75 mM sodium chloride, 0.1% sodium azide, and 0.05% thimerosal, pH 7.0. Antibody working solution is prepared by diluting antibody stock solution at a ratio of 1:80 with antibody diluent.

Figure 3:
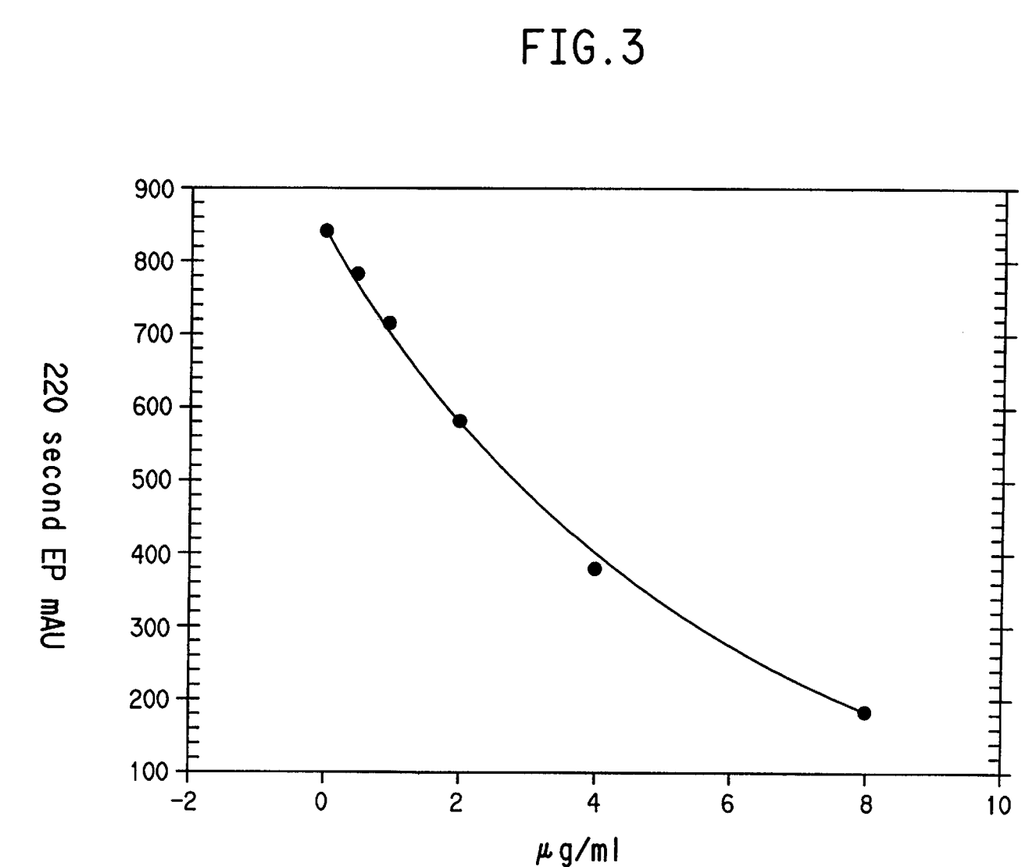
FIG. 3 shows a standard curve in a quinidine turbidimetric inhibition immunoassay. It is more explicitly discussed in Example 6, Part B.

The assay was performed and a standard curve for determining the concentration of quinidine generated using a Cobas® B10 spectrophotometer clinical instrument (Roche Diagnostics, Inc., N.J.) An amount of 5 µL/test of calibration solutions (quinidine standard solutions available from E. I. du Pont de Nemours and Company, Wilmington, Del., for use with the aca® discrete clinical analyzer system, also available from DuPont) was loaded onto the sample wheel of the Cobas® spectrophotometer. An amount of 240 μL/test of particle working solution was loaded into the reagent well of the Cobas® spectrophotometer. An amount of 20 μL/test of antibody working solution was loaded into the start reagent well of the Cobas spectrophotometer. The Cobas was programmed to perform the assay at 37° C. The sample was first mixed and incubated with the particle working solution for 30 seconds. The absorbance at 340 nm was measured and used as blank. An agglutination reaction was then initiated by adding the antibody working solution (start reagent). The endpoint absorbance was measured at 220 seconds. The difference in the two absorbance readings constituted the signal generated by the sample. FIG. 3 shows a plot of endpoint (EP) absorbance (in milliabsorbance units after 220 second) versus the concentration of free quinidine (μg/mL) in the calibrator.

What is claimed is:

1. A process for synthesizing a mono-tert-butoxycarbonyl (t-Boc)-protected hydrophilic diamine reagent, comprising the steps of:

(a) Reacting di-tert butyl dicarbonate with excess hydrophilic diamine in an aqueous and organic medium in the presence of sodium hydroxide;

(b) Separating the organic phase of the medium from the aqueous phase of the medium;

(c) Protonating essentially all of the residual amine groups by reducing the pH of the aqueous phase;

(d) Adding a water-immiscible organic solvent to the aqueous phase to remove nonbasic material from the product of step (c);

(e) Adding base to raise the pH of the aqueous phase such that at least half of the residual amine groups are unprotonated;

(f) Adding salt to aqueous phase of step (e);

(g) Extracting the aqueous phase with a water-immiscible organic solvent;

(h) Separating the organic phase from the aqueous phase; and (i) Removing the solvent from the organic phase to leave the desired product.

2. The process of claim 1 wherein the mono-t-Boc-protected hydrophilic diamine has the structure $Pr-NH(CH_2)_mO(CH_2CH_2O)_n(CH_2)_mNH_2$ where Pr is t-Boc, and m=3 and n=1.

* * * * *